US00PP23417P2

(12) United States Plant Patent
Brennan

(10) Patent No.: US PP23,417 P2
(45) Date of Patent: Feb. 26, 2013

(54) BLACK CURRANT PLANT NAMED 'BEN CHASKA'

(50) Latin Name: *Ribes nigrum*
Varietal Denomination: Ben Chaska

(75) Inventor: Rex M. Brennan, Dundee (GB)

(73) Assignee: James Hutton Institute, Invergowrie (GB)

( * ) Notice: Subject to any disclaimer, the term of this patent is extended or adjusted under 35 U.S.C. 154(b) by 0 days.

(21) Appl. No.: 13/317,787

(22) Filed: Oct. 27, 2011

(51) Int. Cl.
*A01H 5/00* (2006.01)

(52) U.S. Cl. ..... Plt./156

(58) Field of Classification Search ..... Plt./156
See application file for complete search history.

*Primary Examiner* — Annette Para
(74) *Attorney, Agent, or Firm* — Penny J. Aguirre

(57) ABSTRACT

A new cultivar of *Ribes nigrum*, 'Ben Chaska', characterized by its consistent high yields of fruit, its upright and compact growth habit, its high degree of fruit set, its resistance to white pine blister rust and its suitability for machine harvesting and in having a more compact plant habit, larger berries and earlier fruit ripening than 'Ben Como'.

2 Drawing Sheets

Botanical classification: *Ribes nigrum.*
Cultivar designation: 'Ben Chaska'.

CROSS REFERENCE TO A RELATED APPLICATION

This application is co-pending with a U.S. Plant Patent Application filed for a plant derived from the same breeding program that is entitled *Ribes* Plant Named 'Ben Como' (U.S. Plant patent application Ser. No. 13/317,788).

BACKGROUND OF THE INVENTION

The present invention relates to a new and distinct cultivar of *Ribes nigrum* named 'Ben Chaska' and is hereinafter referred to by the cultivar name 'Ben Chaska'. 'Ben Chaska' represents a new cultivar of black currant grown for fruit production.

'The new cultivar was derived from a controlled breeding program by the Inventor in Invergowrie, Scotland. The Inventor made a cross in 1984 between an unnamed proprietary plant in the Inventor's breeding program, reference no. SCRI P10/9/20, as the female parent and 'Polar' (not patented) as the male parent. The Inventor selected 'Ben Chaska', code no. SCRI D16/6/54, in 1986 as a single unique plant amongst the seedlings that resulted from the above cross.

Asexual reproduction of the new cultivar was first accomplished under direction of the Inventor by hardwood cuttings in Dundee, Scotland in 1990. Asexual reproduction of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'Ben Chaska' as a new and unique cultivar of *Ribes nigrum.*

1. 'Ben Chaska' exhibits consistently high yields of fruit.
2. 'Ben Chaska' exhibits an upright and compact growth habit.
3. 'Ben Chaska' exhibits a high degree of fruit set.

4. 'Ben Chaska' exhibits resistance to white pine blister rust (*Cronartium ribicola*).
5. 'Ben Chaska' is readily harvested by machines.
6. 'Ben Chaska' produces a smaller plant, larger berry, and fruit that ripens earlier than 'Ben Como'.

'Ben Chaska' can be readily compared to its parent plants. SCRI P10/9/20, the female parent, differs from 'Ben Chaska' in lacking resistance to white pine blister rust, in being less cold hardy, in having a less compact plant habit, and in exhibiting reduced fruit set. 'Polar', the male parent, differs from 'Ben Chaska' in having a poorer growth rate, in having less consistent and lower fruit yields, and in lacking suitability for machine harvest. 'Ben Chaska' can be most closely compared to the cultivars 'Titania' (U.S. Plant Pat. No. 11,439) and 'Ben Lomond' (not patented). 'Titania' is similar to 'Ben Chaska' in exhibiting resistance to white pine blister rust, but differs from 'Ben Chaska' in having less consistent crop levels, in having a less compact and less manageable plant habit, and in flowering later in the season. 'Ben Lomond' is similar to 'Ben Chaska' in having a high fruit yield, but differs from 'Ben Chaska' in lacking resistance to white pine blister rust, in being less resistant to powdery mildew (*Sphaerotheca mors-uvae*), in having a less compact and less upright plant habit, and in having poorer fruit quality in terms of juice color and flavor. 'Ben Chaska' can also be compared to the cultivar 'Ben Como' (U.S. Plant Patent pending)*, a cultivar from the same breeding program. 'Ben Como' is similar to 'Ben Chaska' in having a consistently high yields, in having a compact and upright growth habit, in degree of fruit set, and in being resistant to white pine blister rust. 'Ben Como' differs from 'Ben Chaska' in flowering slightly later in the season, in having greater vigor, a larger plant size, and in having smaller, later ripening fruit than 'Ben Chaska'.

BRIEF DESCRIPTION OF THE DRAWING

The accompanying colored photographs illustrate the overall appearance and distinct characteristics of the new *Ribes* cultivar. The photographs were taken of five year-old plants of the new cultivar as grown outdoors in a field in Becker, Minn.

The photograph in FIG. 1 provides a view of the habit of 'Ben Chaska' (plants in the front of the row) in comparison to the plant habit of 'Titania' (plants in the back of the row).

Figure 1:
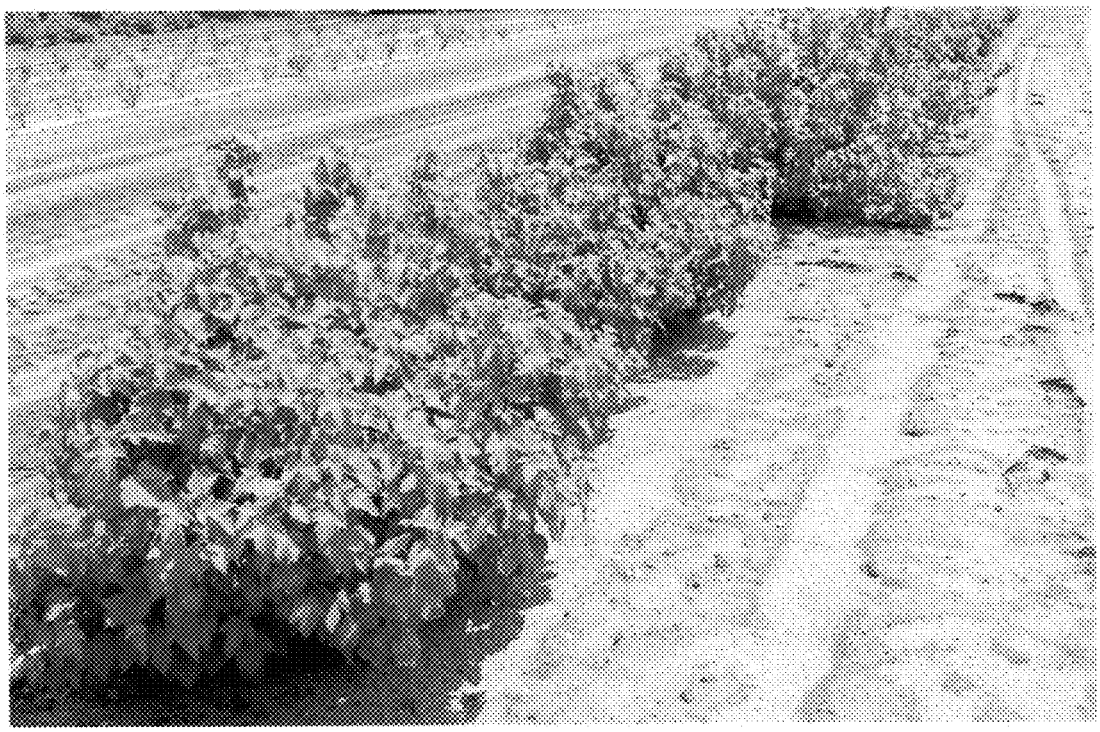
Figure 2:
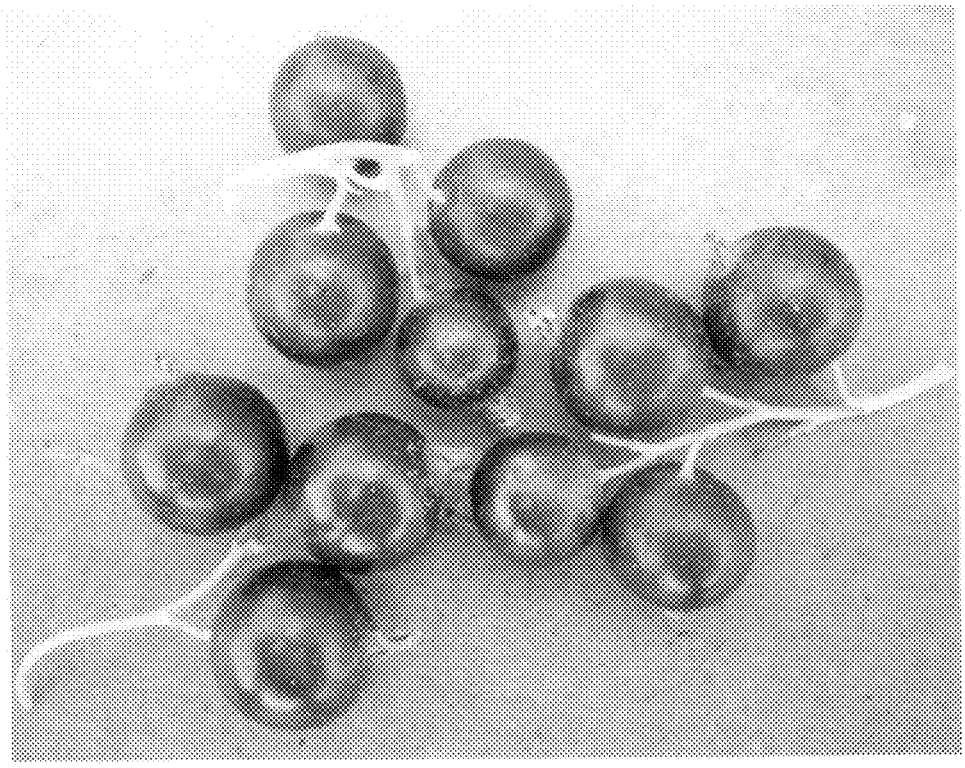

The photograph in FIG. 2 provides a close-up view of the fruit of 'Ben Chaska'.

Figure 3:
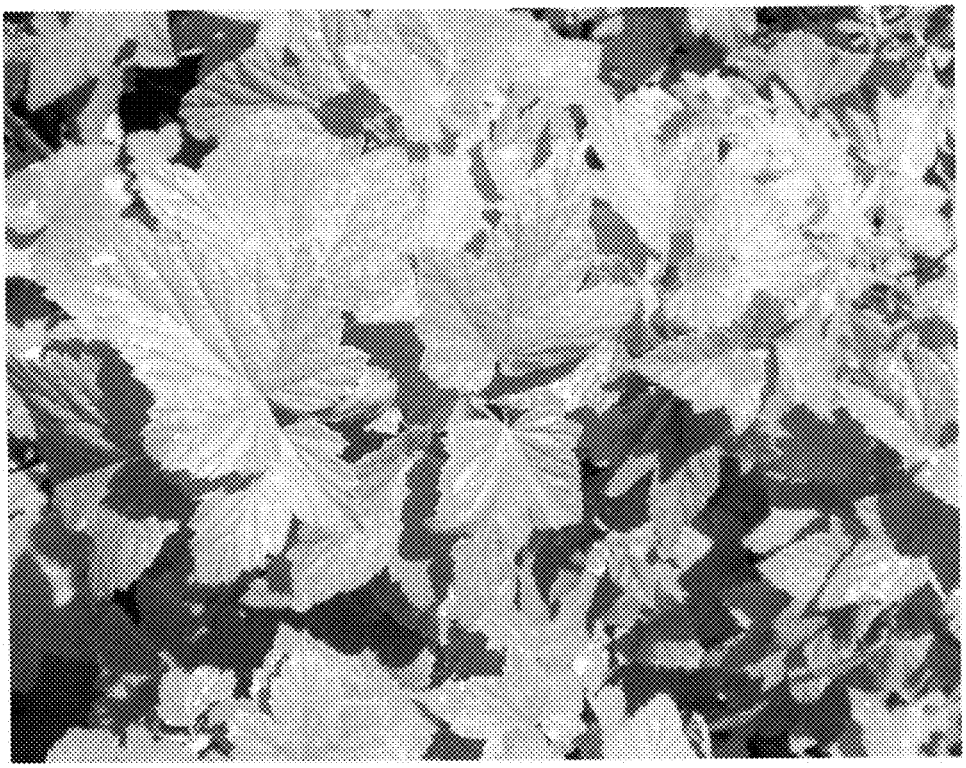

The photograph in FIG. 3 provides a close-up view of the foliage 'Ben Chaska'.

The colors in the photographs are as close as possible with digital photography techniques available, the color values cited in the detailed botanical description accurately describe the colors of the new cultivar of *Ribes*.

DETAILED BOTANICAL DESCRIPTION OF THE PLANT

The following is a detailed description of plants 10 years in age as grown outdoors in a trial field in Becker, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Perennial shrub.

*Plant habit.*—Upright and compact.

*Height and spread.*—Reaches about an average of 1.3 m in height and 2 m in width.

*Cold hardiness.*—U.S.D.A. Zone 3.

*Diseases and pests.*—Observed to be resistant to white pine blister rust (*Cronartium ribicola*) with improved powdery mildew (*Sphaerotheca mors-uvae*) resistance.

*Culture.*—Readily machine harvested.

*Propagation.*—Hardwood cuttings.

*Growth rate.*—Moderate.

New growth description:

*Stem.*—Mature stem 200C in color; new growth N200D in color, surface is glabrous on new growth with smooth bark when mature, main branches up to 1.3 m in length and an average of 7 mm in width.

*Leaf bud shape.*—Obclavate, bracts imbricate.

*Leaf bud size.*—Average 8 mm in length, 3 mm in width.

*Number of buds.*—On 20 cm long stem average of 20 buds, ranging from 6 to 30 buds, per stem.

*Bracts.*—Deltoid in shape, apex retuse to subacute, base truncate, average 5 mm in width, 5 mm in length, turning dry and papery, margin entire and fimbriate, inner surface 52C in color and 56A towards base, turning 164A when dry, outer surface 51A in color and 51D towards base turning 164A when dry, glabrous on inner surface, glandular on lower surface; glands <1 mm in diameter, round in shape, 14B in color.

Foliage description:

*Leaf shape.*—Ovate.

*Leaf division.*—Simple.

*Leaf base.*—Cordate to auriculate.

*Leaf apex.*—Subacute.

*Leaf venation.*—Pinnate, color on upper and lower surface 145B.

*Leaf margins.*—3 to 5 lobed to palmatifid with lobe margins serrate.

*Leaf attachment.*—Petiolate.

*Leaf arrangement.*—Alternate clusters of 8-12 leaves, cluster base sheathed by bracts averaging 6 mm in length and 4 mm in width, N199D to 166D in color.

*Leaf orientation.*—Upright to 20 degree from main stem.

*Leaf surface.*—Upper surface glabrous, lower surface slightly puberulent with fine minute hairs and glandular.

*Leaf color.*—Upper surface, ranges from 139B to 141B; lower surface ranges from 138B to 137C.

*Leaf size.*—Average of 2.8 cm in length, ranging from 1 cm to 4.5 cm; average of 3.2 cm in width, ranging from 1 cm to 4.5 cm in width.

*Leaf quantity.*—About 82 per 30 cm stem.

*Petioles.*—Round in shape, an average of 4 cm in length and 1 mm in width, ranging from 0.6 to 6 cm in length, 144A in color, minutely puberulent.

*Stipules.*—None observed.

Inflorescence description:

*Bloom season.*—Approximately April 20 to May 1 in Becker, Minn.

*Inflorescence.*—Drooping raceme, average 3.5 cm in length 1.8 cm in width, densely pubescent with minute hairs, 10 racemes per 30 cm long stem.

*Lastingness of inflorescence.*—5 to 12 days depending on weather conditions at time of bloom.

*Pedicels.*—Round 1 mm in width, 2 to 8 mm in length, 145B in color, surface has sparse hairs, minute bract at base of pedicel <1 mm in length and width.

*Peduncles.*—Round, an average of 3 cm in length and 2.5 mm in width, surface has sparse hairs, 145B in color.

*Flowers.*—Globular, campanulate, 3 to 10 flowers per raceme.

*Flower size.*—Average of 6 mm in length, 6 mm in width.

*Flower buds.*—Globose in shape, 2 to 4 mm in length and width, 144B in color.

*Sepals.*—Five, strongly recurved, 2 mm in width, 6 mm in length fused at base, color 144A on upper surface and 144B on lower surface, rounded apex, margins entire, sparsely pubescent on upper surface and pubescent on lower surface.

*Petals.*—Five fused in hypanthium, 3 mm in length, 2 mm in width, 157B in color on upper and lower surface, glabrous on upper and lower surface.

*Androecium.*—Epipetalous, anthers are basifixed, 158B to 160B in color, 1 mm in length and 0.5 mm in width, filaments are 2 mm in length, <0.5 mm in width, and 144B in color.

*Gynoecium.*—1 pistil, style is 4 mm in length, 1 mm in width, and 144D in color, ovary is inferior, 4 mm in length, 4 mm in width, globose in shape, and 144D in color, stigma is minute, bifid, and 144D to N137A in color.

Fruit description:

*Fruit number.*—16 to 30 fruits per branch 30 cm in length.

*Fruit yield.*—1.6 kg per plant at Becker Minn. on 5 year old plants (compare to 2.7 kg for 'Ben Como' and 2.2 for 'Titania').

*Fruit set.*—High, 65 to 80%.

*Fruit size.*—1.4 cm in diameter and height.

*Fruit weight.*—Average of 129.7 g/100 berries.

*Fruit chemistry.*—Averages: Brix 15.4, specific gravity 1.0644, acidity 3.303 g/L tartaric and 3.9084 g/L citric, anthoncyanins 1.526 (430 nm), 3.095 (515 nm), 0.646 (580 nm), ascorbic acid 72.25 ml/100 ml.

*Position of maximum diameter.*—Midway between proximal and distal ends.

*Fruit shape.*—Globose.

*Fruit symmetry.*—Symmetric.

*Persistence of calyx.*—Persistent at harvest, 200D in color, 3 mm in length.

*Surface.*—Glossy, smooth except for slightly protruding lenticels.

*Lenticels.*—60 to 80 per fruit, 200D in color.

*Waxiness of skin.*—Weak.

*Thickness of skin.*—Thin.

*Skin color.*—Immature 187A, mature 202A.

*Color of flesh.*—Blend of 195B to 195C.

*Fruit maturity date.*—Late June.

*Seed.*—Ovate, 40 per fruit, 2 mm in length, 1.5 mm in width, 165C in color.

*Firmness (without skin).*—Soft.

*Texture of flesh.*—Pulpy, juicy.

*Cropping frequency.*—Annually.

*Flavor.*—Sweet and acid.

It is claimed:

1. A new and distinct cultivar of Black Currant plant named 'Ben Chaska' as herein illustrated and described.

* * * * *